United States Patent  (10) Patent No.: US 7,695,533 B2
Kovács et al.  (45) Date of Patent: Apr. 13, 2010

(54) METHOD FOR TRANSESTERIFYING VEGETABLE OILS

(75) Inventors: András Kovács, Budapest (HU); Lóránt Haas, Budapest (HU); István Gòczi, Budapest (HU); Gyula Szabó, Budakalász (HU); Mária JámbornéUlbrecht, Tököl (HU)

(73) Assignee: Quicksilver Limited, London (GB)

( * ) Notice: Subject to any disclaimer, the term of this patent is extended or adjusted under 35 U.S.C. 154(b) by 600 days.

(21) Appl. No.: 10/495,098

(22) PCT Filed: Nov. 8, 2002

(86) PCT No.: PCT/HU02/00114

§ 371 (c)(1), (2), (4) Date: May 7, 2004

(87) PCT Pub. No.: WO03/040081

PCT Pub. Date: May 15, 2003

(65) Prior Publication Data

US 2005/0016059 A1  Jan. 27, 2005

(30) Foreign Application Priority Data

Nov. 8, 2001  (HU) .................................. 0104786

(51) Int. Cl.
*C10L 1/18*   (2006.01)
(52) U.S. Cl. .......................................... 44/308; 44/388
(58) Field of Classification Search ............ 44/307, 44/308, 311, 385, 386, 388, 605, 905
See application file for complete search history.

(56) References Cited

U.S. PATENT DOCUMENTS 2,360,844 A  10/1944  Bradshaw et al.

(Continued)

FOREIGN PATENT DOCUMENTS

CA  2131654 A1  3/1996

(Continued)

OTHER PUBLICATIONS

Darnoko, D. et al. "Continuous Production of Palm Methyl Esters," *Journal of the American Oil Chemists' Society*; vol. 77, No. 12; pp. 1269-1272 (Aug. 2000).

(Continued)

*Primary Examiner*—Cephia D Toomer
(74) *Attorney, Agent, or Firm*—Janet Sleath; Speckman Law Group PLLC

(57) ABSTRACT

The present invention relates to a method for producing Diesel grade fuel of plant origin by transesterifying a refined vegetable oil in a homogenous phase with a C1-C4 alkanol in the presence of an aliphatic hydrocarbon solvent with a boiling point of 40-200° C. and a catalyst to form a first polar phase comprising glycerol by-product and a first apolar phase comprising transesterified fuel, non-transesterified vegetable oil, and aliphatic hydrocarbon solvent, separating the first polar phase and the first apolar phase, and refining the fuel from the first apolar phase, wherein the C1-C4 alcohol is used in an amount selected from the group consisting of: a stoichiometric amount; and an excess not exceeding 30% of an stoichiometric amount, and the aliphatic hydrocarbon solvent is used in an amount of at least 0.2 parts by volume relative to the unit volume of the refined vegetable oil.

18 Claims, 1 Drawing Sheet

U.S. PATENT DOCUMENTS

Figure 1:
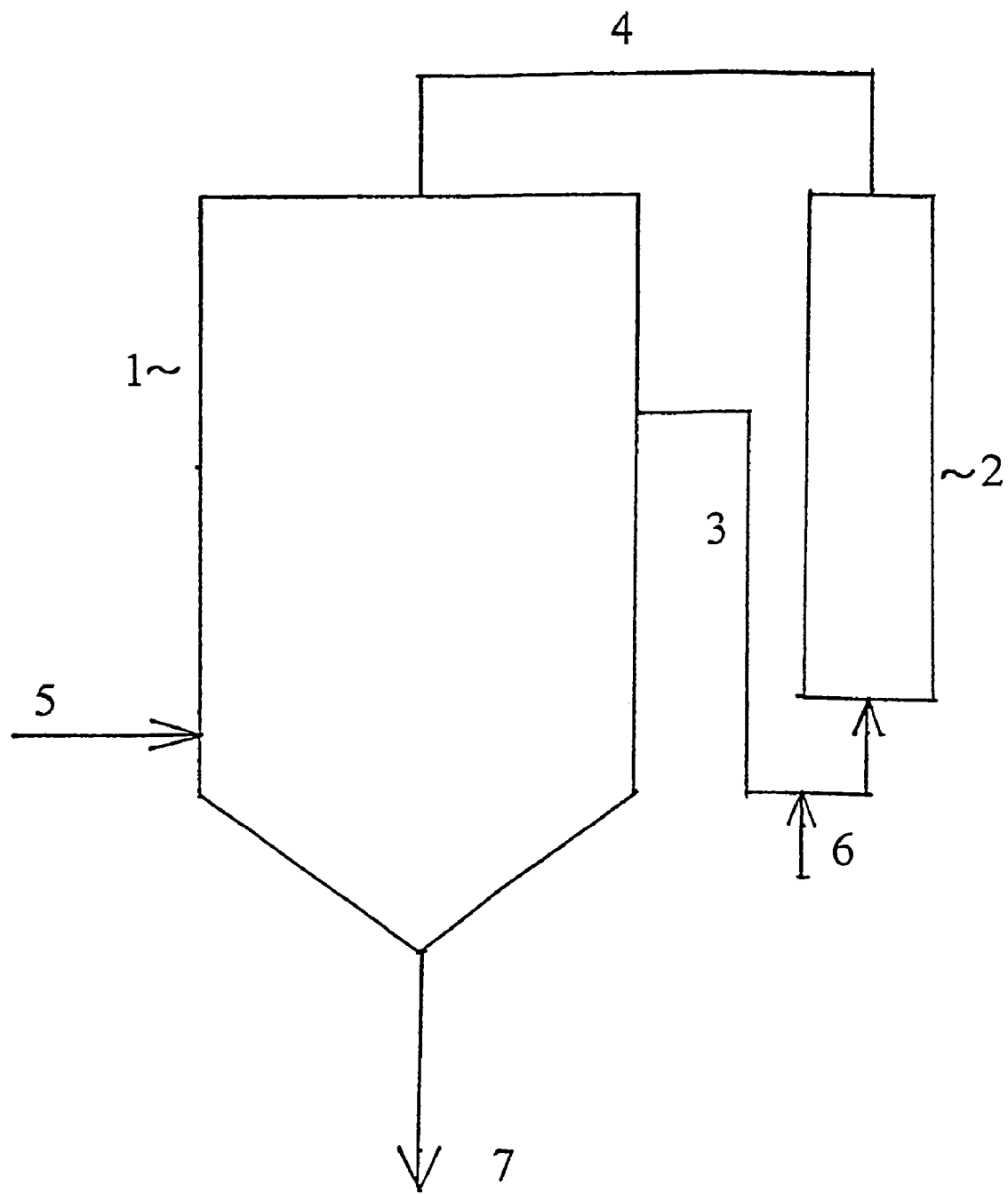

| | | | |
|---|---|---|---|
| 2,383,632 A | 8/1945 | Trent | |
| 2,383,633 A | 8/1945 | Trent | |
| 4,695,411 A * | 9/1987 | Stern et al. | 554/167 |
| 5,219,733 A * | 6/1993 | Myojo et al. | 435/52 |
| 5,354,878 A * | 10/1994 | Connemann et al. | 554/167 |
| 5,424,467 A * | 6/1995 | Bam et al. | 554/216 |
| 5,520,708 A | 5/1996 | Johnson et al. | |
| 5,697,986 A * | 12/1997 | Haas | 44/308 |
| 6,015,444 A | 1/2000 | Craft et al. | |

FOREIGN PATENT DOCUMENTS

| | | |
|---|---|---|
| DE | 42 09 779 C1 | 7/1993 |
| WO | WO 01/12581 A1 | 2/2001 |

OTHER PUBLICATIONS

Hoffman, G. "Chemistry and Technology of Edible Oils and Fats and Their High Fat Products," pp. 144-145, Academic Press: London/Toronto (1989).

"Production of a cost-competitive biodiesel fuel alternative to petroleum diesel," *Environmental Science and Engineering*, May 2001, www.esemag.com.

* cited by examiner

METHOD FOR TRANSESTERIFYING VEGETABLE OILS

FIELD OF THE INVENTION

The invention relates to improvements in or relating to a method for transesterifying vegetable oils. More particularly, the invention relates to an improved method for producing Diesel grade fuel of plant origin (also referred to in the following as biodiesel fuel or biodiesel) by transesterifying vegetable oils with C1-C4 alkanols (also referred to in the following as alkanols).

BACKGROUND OF THE INVENTION

It is known that transesterification of vegetable oils with an alkanol has a decisive influence on the quality of fuels produced from the oils, because the transesterification reaction determines whether the viscosity of the resulting fuel suitable for use in fuel-injection engines.

Transesterification of vegetable oils with an alkanoi proceeds in a reversible, equilibrium reaction according to the following scheme:

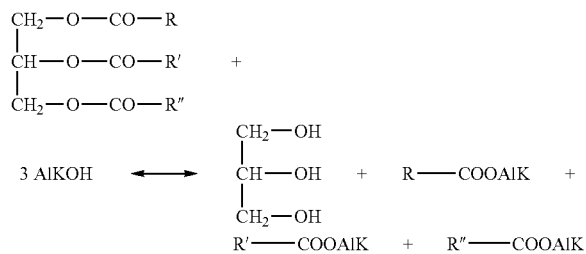

in the above formula, R, R' and R" stand for the hydrocarbyl moieties of the fatty acid constituents of vegetable oils and Alk is a C1-C4 alkyl group. As shown in the above scheme, glycerol is formed as a by-product in the reaction in addition to the fatty acid methyl esters, which are usable as fuel. The equilibrium can be shifted towards the formation of the required fatty acid alkyl esters by increasing the amount of the alkanol reactant and/or by removing the glycerol by-product. Transesterification is performed generally in the presence of a catalyst. Usually bases are applied as catalysts (most frequently potassium hydroxide); acid catalysts are used less frequently. Methanol is the most frequently used alkanol.

A standard method for transesterifying vegetable oils using methanol and for producing biodiesel fuel are disclosed in U.S. Pat. Nos. 2,360,844, 2,383,632 and 2,383,633. This method has been generally used, with some minor modifications, for the production of biodiesel fuel on industrial scale until now. According to the method disclosed in the cited references, vegetable oil is reacted with methanol in the presence of potassium hydroxide catalyst for at least one hour at a temperature below the boiling point of methanol (usually at 65° C.). As methanol and vegetable oil have only limited miscibility in each other, the biphasic reaction mixture is intensely stirred and/or phase transfer catalysts are used in order to accelerate the reaction. Glycerol, which is liberated as a by-product, accumulates in the polar (methanol) phase, and—in accordance with the equilibrium nature of the reaction—is prone to reconvert the once-produced fatty acid methyl esters into glyceride esters. The optional phase transfer catalyst also contributes to this reconversion process, thus no full conversion of the vegetable oil can be attained. When the reaction mixture is close to equilibrium, which corresponds to a conversion rate of about 80%, the mixture is allowed to settle for about one day. Thereafter, the lower polar phase (which comprises glycerol together with the major portion of methanol used in excess) is removed, and the reaction is repeated with the upper apolar phase with freshly admixed alcohol and catalyst. After this second step, the upper apolar phase (fuel phase) is separated again, subjected to distillation to remove part of the methanol contained therein, washed with aqueous sulphuric acid to remove potassium hydroxide, washed again with water, dried and filtered (this latter series of operations is to refine the biodiesel fuel). If desired, quality improving additives, particularly additives improving cold resistance, are added to the resulting biodiesel fuel.

Major disadvantages of the above method are as follows: due to the biphasic mixture, the reaction requires a lengthy period of time and an energy consuming intense stirring to proceed; separation of the phase which contains the glycerol by-product is difficult and extremely time consuming; methanol is used in a great excess to the stoichiometric amount in order to shift the reaction towards the formation of the required product; the majority of non-reacted methanol appears in the glycerol phase from which it cannot be recovered in an economic way unless acceptable operational capacity is employed. In a paper discussing the improvement potentials of biodiesel transesterification fuel production (*D. Darnoko and M Cheryan: JAOCS* 77, 1269-1272 (December, 2000)), the authors mentioned further disadvantages in that the method requires large reactor volumes and repeated start up/shut down cycles, resulting in increased in capital and labour investments and decreased in production efficiency, and furthermore, the quality of the product may vary from batch to batch.

According to U.S. Pat. Nos. 5,520,708 and 6,015,444, the time required for transesterification and phase separation is reduced by performing the reaction in an assembly of a static mixer, a heat exchanger, a homogenizer and a settling vessel rather than using a conventional reaction vessel equipped with a stirrer. The static mixer used in this method, like all static mixers, does not contain moving means for mixing the reactants; a turbulent flow created either by flow-breaking means (such as baffles, ribs, coils etc.) mounted inside the mixer or by a packing filled into the mixer serves to mix the reactants intensely. Vegetable oil, alkanol (most frequently methanol) and catalyst are passed through the static mixer, and the resulting dispersed stream is heated to reaction temperature in the heat exchanger. Thereafter the mixture is subjected to a high shear in the homogenizer to form an emulsion, and the emulsion is passed into the settling vessel where no further stirring is applied. The lifespan of the emulsion formed in the homogenizer enables transesterification to proceed to equilibrium conversion before the emulsion segregates in the settler. Although a significant reduction in time requirement can be attained with this method, it has a disadvantage in that a homogenizer with high energy consumption is used. Again, a conversion rate higher than the equilibrium in a single step may not be attained by using this method. Thus, in order to attain 95-98% conversion rate, which is required to obtain a fuel product with appropriate viscosity, the apolar phase needs to be reacted once again after the first step. A great excess of alkanol needs to be used, which is unacceptable for industrial scale production.

According to the method disclosed in DE 42,09,779, 98% conversion of vegetable oil is attained by performing transesterification in a column divided into reaction zones and separation zones, wherein each reaction zone is followed by a separation zone. The vegetable oil, the alkanol and the catalyst are fed into the first reaction zone. After a prescribed period of time, the resulting mixture is fed into the first separation zone and the glycerol is removed by centrifugation. The resulting glycerol-free mixture is then fed into the second reaction zone, and the above reaction/separation steps are repeated in series until the required rate of conversion is attained. An important advantage of this method is that it can also be performed as a continuous operation, because the time consuming step of settling the mixture is replaced by the much faster step of centrifugal separation. This advantage is, however, overcompensated by the extremely high installation costs which render the method too expensive. Therefore, this method is not employed in plants which have a capacity lower than 100,000 tons/year. As a further disadvantage, this method cannot be applied for transesterifying vegetable oils containing more than 2% of free fatty acids.

In order to avoid the disadvantages associated with heterogeneous reactions, particularly in order to decrease reaction time and energy demand of stirring, a method to transesterify vegetable oils with alkanol under homogeneous reaction conditions has been suggested. [www. bioxcorp.com with reference to Production of a cost-competitive biodiesel fuel alternative to petroleum diesel, in *Environmental Science & Engineering*, May, 2001.]. According to this method, a polar solvent that is highly soluble both in the polar alkanol and in the apolar vegetable oil (such as tetrahydrofuran or N-methyl-2-pyrrolidin-one) is utilized as a reaction medium. However, such a method requires very complicated and energy consuming separation steps for processing the final reaction mixture, which overcompensates the advantages resulting from the use of a homogeneous mixture. Specifically, due to a change in phase conditions after transesterification, the polar solvent is distributed between the biodiesel phase with increased apolarity and the glycerol phase with increased polarity and needs to be removed from both phases. The disadvantages arising from the equilibrium nature of the reaction cannot be avoided with this method, since glycerol is continuously present in a reactive state in the reaction mixture for transesterification. Thus, this solvent assisted method has not been utilized on an industrial scale.

Publications relating to biodiesel fuel production generally state that efficient transesterification, which is imperative for obtaining a product having the required quality, requires the use of refined vegetable oil as a starting substance. This is particularly important when the vegetable oil is a waste (e.g. used frying oil). No specific method for refining vegetable oils has been disclosed, however, in publications relating to biodiesel fuel production. According to the known technologies for producing food grade products, vegetable oils are refined by treating them with water to remove hydratable phospholipids and with a cids, such as phosphoric acid or citric acid, to remove non-hydratable phospholipids [*Hoffman, G.: Chemistry and technology of edible oils and fats and their high fat products*, Academic Press, London ; Toronto, 1989]. The resulting refined vegetable oils (termed in food technology as "degummed oils") are suitable to be used as starting substances for biodiesel fuel production. From the aspect of transesterification proceeding in heterogeneous phase, it is an advantage that such refined (degummed) vegetable oils contain a series of minor components having some surfactant properties. In the method of U.S. Pat. Nos. 5,520,708 and 6,015,444, these vegetable oil components are utilized to form an emulsion. However, the difficulties in the separation of the apolar phase comprising transesterified substances from the polar phase comprising glycerol by-product can be attributed to the presence of these components.

It would therefore be desirable to provide improvements in transesterification, which is a key step in biodiesel fuel production. The present invention provides a method which enables one to reduce considerably the time requirements of transesterification and subsequent glycerol removal without requiring expensive equipment or complicated processing steps. The present invention further provides a method which enables one to reduce considerably the alkanol requirement of the transesterification reaction without affecting the conversion rate and to attain the required conversion rate of 95-98% without the time-consuming intermittent glycerol separation steps.

SUMMARY OF THE INVENTION

It has been found, unexpectedly, that the present invention may be achieved fully when an aliphatic hydrocarbon, either a cycloaliphatic hydrocarbon, or a cycloaliphatic-aliphatic hydrocarbon with a boiling point of 40-200° C. or a mixture of such hydrocarbons is used as a reaction medium in the alkanol transesterification of the vegetable oil, in an amount of at least 0.2 parts by volume of hydrocarbon(s) relative to the unit volume of the starting refined vegetable oil.

The present invention provides an improved process for producing Diesel grade fuel of plant origin by transesterifying a refined vegetable oil with a C1-C4 alkanol in the presence of a catalyst whereupon a polar phase and an apolar phase is formed. The polar phase which comprises glycerol by-product is next removed, and the apolar phase which comprises the fuel is subjected to a refining procedure. According to the present invention, the refined vegetable oil is transesterified in a homogeneous phase in the presence of at least 0.2 parts by volume, relative to the unit volume of refined vegetable oil, of an aliphatic hydrocarbon solvent with a boiling point of 40-200° C. to form a mixture comprising a polar phase and an apolar phase. If necessary, the apolar phase, which also comprises non-transesterified vegetable oil besides the aliphatic hydrocarbon solvent and the transesterified product, and is obtained after removing the separated polar phase comprising glycerol by-product, is reacted in a further step with a C1-C4 alkanol in the presence of a catalyst until a transesterification conversion of 95-98% is attained. The separated polar phase comprising the glycerol by-product is then removed, and the apolar phase comprising the fuel is refined.

Thus, the basic difference between the method according to the present invention and the known methods wherein transesterification is performed in a homogeneous reaction mixture, is that a specific apolar solvent, instead of a polar solvent, is used to form the homogeneous reaction mixture. The aliphatic hydrocarbons used as apolar solvents according to the present invention have the unique property that they can dissolve the required amount of polar alkanol used in the reaction, but they dissolve the glycerol by-product (which is also an alcohol and also a polar substance) to a very limited degree. Thus the mixture for transesterification remains homogeneous during the full course of the reaction, which enables the reaction to proceed quickly. At the same time, as the reaction proceeds, glycerol accumulates in a distinct polar phase, which fully separates from the apolar phase within a short period of time. By an appropriate feeding of the alkanol to the reaction, only a small amount of alkanol is dissolved in the polar phase. Thus only a small loss in alkanol is caused by the removal of the polar phase, whereby, the amount of alkanol required in transesterification may be reduced significantly.

BRIEF DESCRIPTIONS OF THE DRAWINGS

Further advantages and embodiments of the present invention are explained in the following description with reference to the attached drawing, wherein:

FIG. 1 shows an assembly of the present invention wherein the transesterification and separation process of the polar and apolar phases are performed.

DETAILED DESCRIPTION OF THE INVENTION

According to the present invention, the transesterification reaction is performed at a temperature of 60-140° C., preferably at 95-115° C., under a pressure sufficient to maintain the alkanol in liquid state. Any of the conventional catalysts usable for transesterification may be used in the transesterification method of the present invention. Potassium hydroxide is a particularly preferred catalyst. The pressure of the reaction may be 1-40 bar.

The lower limit of the amount of the aliphatic hydrocarbon solvent employed is a critical value. It has been observed that the minimum amount of aliphatic hydrocarbon solvent required to form a homogeneous phase in transesterification varies with the nature of the starting vegetable oil and with the method used to refine the vegetable oil. When the vegetable oils are refined according to the method of the present invention, described below, 0.2 parts by volume of aliphatic hydrocarbon solvent may be sufficient to form a homogeneous phase in transesterification, whereas when the vegetable oils are refined by other methods (e.g. by an aqueous-acidic treatment as discussed above), the minimum amount of aliphatic hydrocarbon required to form a homogeneous phase in transesterification may be greater (usually 0.3-0.4 parts by volume, related to unit volume of the refined plant oil). The required minimum amount of aliphatic hydrocarbon solvent can easily be determined experimentally. It has been observed that when the amount of the aliphatic hydrocarbon solvent is raised above the critical lower limit, the time required for full separation of the polar and apolar phase decreases. Unlike the lower limit, the upper limit of the amount of the aliphatic hydrocarbon solvent is not a decisive factor in transesterification, and the amount depends primarily on economic considerations. No particular advantages have been found to arise from raising the amount of the aliphatic hydrocarbon solvent above two-fold the amount of the starting refined vegetable oil. The volume ratio of the starting refined vegetable oil to the aliphatic hydrocarbon solvent is preferably 1:(0.2-1.5), more preferably 1:(0.3-1), and most preferably 1:(0.4-0.7).

Aliphatic hydrocarbon solvents preferably having boiling points of 60-180°, or mixtures of such solvents are preferably used (when a mixture is used, the figures represent boiling ranges). Mineral oil cuts of low aromatic content having boiling point ranges of 60-100° C., 100-140° C., and 140-180° C. are particularly preferred.

An upper apolar phase may be obtained by mixing a solution containing a non-refined vegetable oil, an aliphatic hydrocarbon solvent having a boiling point range of 40-200° C., and aqueous glycerol, and allowing the mixture to settle. This upper apolar phase is preferably used in the process according to the present invention instead of a mixture that contains refined vegetable oil and aliphatic hydrocarbon solvent as separate streams. The upper apolar phase is in fact a solution of refined vegetable oil in the respective aliphatic hydrocarbon solvent. In a vegetable oil refining method, which is adapted specifically to the transesterification method of the present invention, a unit volume of non-refined vegetable oil is thoroughly mixed with at least 0.2 parts by volume (preferably 0.2-1.5, more preferably 0.3-1, and most preferably 0.4-0.7 parts by volume) of an aliphatic hydrocarbon solvent with a boiling point of 40-200° C. and with 0.07-0.2 parts by volume (preferably 0.09-0.15 parts by volume) of aqueous glycerol comprising 5-40% by volume (preferably 10-20% by volume) of water. The mixture is allowed to settle to form a lower polar phase and an upper apolar phase, and the upper apolar phase, which is a solution of the refined vegetable oil in the aliphatic hydrocarbon solvent, is then transferred to transesterification. Using this refining method, impurities and components which may disturb transesterification and subsequent separation are removed from the vegetable oil much more efficiently than by the known method discussed above. Also, minor components with surfactant properties, which cannot be removed from the vegetable oil with the conventional aqueous-acidic refining, are removed using the vegetable oil refining method according to the present invention, which further accelerates the separation of the polar and apolar phases formed during the transesterification process. A further important advantage of this oil refining method is that no foreign substance is introduced into the process, since the aliphatic hydrocarbon solvent is utilized as the reaction medium in transesterification, and the glycerol is the by-product formed in transesterification.

Transesterification according to the present invention may be performed in a reaction vessel, usually in an autoclave equipped with a stirrer and with a heating jacket conventionally used for transesterification, according to the two-step method well known in the art. The aliphatic hydrocarbon solvent, the refined vegetable oil (or a preformed solution thereof, e.g. the upper apolar phase obtained in the above refining step), the alkanol and the catalyst (or a preformed solution thereof) are introduced into the vessel, and the mixture is stirred at the prescribed reaction temperature. When the reaction is performed under atmospheric pressure, the temperature of the reaction must not exceed the boiling point of the alkanol. However, the reaction can also be performed at higher temperatures under superatmospheric pressure, provided that the alkanol remains in liquid state. The reaction may be performed at a temperature of 60-140° C. under a pressure of 1-40 bar. By applying elevated temperature under superatmospheric pressure, the speed of reaction may be further increased. When transesterification reaction has reached the steady (equilibrium) state, heating and stirring is stopped, pressure is reduced to atmospheric if necessary, and the phases are allowed to separate. The steady state sets in within a short time (sometimes within 10 minutes), and the separation of the phases is also quick (full separation occurs sometimes within 10 minutes). The polar lower phase, consisting mainly of glycerol together with a small amount of alkanol, is removed and may be subjected to known glycerol processing operations, if desired. The upper apolar phase, which contains some unreacted vegetable oil together with the aliphatic hydrocarbon solvents and the fatty acid alkyl esters formed in transesterification, is then subjected to a second transesterification step as described above to attain the required 95-98% conversion rate. Again, the required reaction time is short (sometimes less than 10 minutes). Full separation of the polar lower phase formed in this second step from the upper a polar phase usually takes a longer period of time. However, the full separation still takes much less time than that required in the conventional method. If desired, phase separation may be accelerated by known methods (e.g. by filtering the biphasic mixture through a particulate, porous or sieve-like substance with a solid/liquid surface tension of at least 40 mN/m, such as basalt filling, cotton, metal sieve or ion exchange resin).

In the first transesterification step a conversion rate of 85-88% (i.e. exceeding somewhat the obtainable rate in the conventional method) can usually be attained, despite the fact that the excess of alkanol, if any, is not higher than 30% relative to the stoichiometric amount. A higher excess of alkanol is not required.

Transesterification and separation of the polar and apolar phases are preferably performed in an assembly as shown in FIG. 1, which comprises a receiver 1 and a static mixer 2 which has a volume smaller than that of the receiver 1. The static mixer 2 is coupled to the receiver 1 as a bypass via pipelines 3 and 4. The receiver 1 serves to receive the aliphatic hydrocarbon solvent and the reactants required for transesterification, or it may receive only the refined vegetable oil and the aliphatic hydrocarbon solvent. The receiver 1 also serves to separate the polar and apolar phases from one another, whereas the actual transesterification reaction takes place in the static mixer 2. In the receiver 1, temperature and pressure are adjusted to ambient values, whereas the static mixer 2 is heated to the prescribed reaction temperature. If the temperature is higher than the boiling point of the alkanol under atmospheric pressure, the pressure prevailing in the static mixer 2 is adjusted with a pressurizing unit (not shown in the FIGURE) to a value required for keeping the alkanol in liquid state. In this embodiment, a pressure reducer (not shown in the FIGURE) is installed into pipeline 4 at a point before it enters the receiver 1. In the static mixer 2, the temperature may be adjusted to 60-140° C. (preferably to 95-115° C.), whereas the pressure may be adjusted to 1-40 (preferably to 20-24 bar). The refined vegetable oil and the aliphatic hydrocarbon solvent (preferably as the upper phase obtained in the vegetable oil refining step according to the present invention) are fed into the receiver 1 at a point shown by arrow 5 in FIG. 1. If desired, the alkanol and the catalyst may also be fed into the receiver 1, however, it is more preferred to introduce the alkanol and the catalyst at a point shown by arrow 6 into pipeline 3, which connects the receiver 1 to the static mixer 2, before the pipeline 3 enters the static mixer 2. During the transesterification process, portions of the mixture fed into the receiver 1 are circulated through the static mixer 2 at a rate which enables the transesterification to proceed at least partially in the static mixer 2. When the alkanol and catalyst are not fed into the receiver 1, these substances are fed into the stream exiting the receiver 1 at a point shown by arrow 6. A substance stream may also be fed batchwise from the receiver 1 into the static mixer 2. Alkanol and catalyst may be fed into this stream at a point shown by arrow 6, and after an appropriate period of time the substance stream in the static mixer 2, which comprises aliphatic hydrocarbon solvent, fatty acid alkyl esters, some non-transesterified vegetable oil, glycerol, catalyst, and optionally a small amount of alkanol, may be reintroduced into the receiver 1. This procedure may be repeated again. It is, however, preferable to feed a substance stream continuously from the receiver 1 into the static mixer 2 at a rate which enables transesterification to proceed at least partially in the static mixer 2. The term "circulated through the static mixer" encompasses both solutions. If the alkanol and catalyst are fed at the point shown by arrow 6, the total amount of alkanol required for transesterification is preferably introduced into the substance stream in portions so that during the initial stage of transesterification, the mixture in the static mixer 2 contains the alkanol only in a stoichiometric amount or less, and the amount of added alkanol is raised above the stoichiometric value only when a relatively high conversion (preferably above 80%) has already been attained. This transesterification operation may be repeated until the required 95-98% conversion rate is attained.

Since the conditions prevailing in the receiver 1 differ from those prevailing in the static mixer 2, and the mixture in the receiver 1, from which the polar glycerol phase rapidly separates is not stirred, the transesterification reaction generally cannot proceed in the receiver 1, and if it does proceed, the reaction proceeds very slowly. Thus, the glycerol, separated as a distinct phase in the receiver 1, cannot react in the receiver 1 with the fatty acid alkyl esters to reform the vegetable oil. Thus, as a result of the continuous separation of glycerol, the transesterification reaction is shifted towards the formation of the required fatty acid alkyl esters, and the required 95-98% conversion rate can be attained without stopping transesterification separating the phases, and repeating transesterification in a further step with the apolar upper phase. Also, no significant alkanol excess is required to attain 95-98% conversion. If the alkanol is introduced into the static mixer 2 as a separate stream in portions, so that in the initial stage of transesterification less than stoichiometric amounts are introduced and the amount of the added alkanol is raised only after attaining a relatively high conversion, a 95-98% conversion may be attained even upon using the alkanol in stoichiometric amount. A further important advantage of this method is that it may be performed in a very simple apparatus. If desired, depending on the dimension of the receiver 1, portions of the separated polar phase may be removed from the receiver 1 periodically during transesterification.

When the required 95-98% conversion has been attained, transesterification is stopped, the substance in the receiver 1 is allowed to settle, and the lower polar phase consisting mainly of glycerol is removed. A portion of the removed glycerol can be recycled in the vegetable oil refining step after admixing it with the required amount of water. If a vegetable oil refined according to the method of the present invention is used in transesterification, the purity grade of the resulting glycerol phase will be higher than that attainable by the conventional method, resulting in easier further processing. This is an additional advantage of the method of the present invention.

The upper apolar phase obtained at the end of transesterification, which comprises the required biodiesel fuel, is then subjected to refining operations. Conventional steps of refining may be applied. The aliphatic hydrocarbon solvent may also be removed upon refining. However, in some instances, particularly when aliphatic mineral oil having higher boiling ranges is employed, it is preferable to retain at least a portion of the aliphatic hydrocarbon solvent in the biodiesel fuel product, because these components improve the quality of the fuel (e.g. increasing its octane number and decreasing its iodine number).

A preferred method of refining is described below.

Refining of the upper apolar phase: The small amount of alkanol is removed by distillation, thereafter the apolar phase is washed with dilute aqueous sulfuric acid and then with water. The water is removed by azeotropic extractive distillation. Finally, if desired, the aliphatic hydrocarbon solvent or a part thereof is distilled off. The presence of the aliphatic hydrocarbon solvent considerably simplifies the removal of water during the refining process.

Refining of the lower polar phase: The alkanol is removed by distillation and the catalyst is removed by a method fitting the nature of the particular catalyst (e.g. potassium hydroxide catalyst may be removed as potassium sulfate by sulfuric acid treatment). When neat glycerol is to be prepared, the polar phase is passed through anion and cation exchange resins. If water has been introduced during refining, it may be removed most efficiently by azeotropic distillation performed in the presence of the aliphatic hydrocarbon solvent and subsequent removal of the solvent residues by distillation.

The presence of aliphatic hydrocarbon solvent facilitates refining, too, since in its presence, both glycerol and the apolar phase can be dried (dehydrated) by simple atmospheric distillation. The alkanol and the aliphatic hydrocarbon solvent may be recovered easily in the refining operation and may be recycled into the transesterification step. Portions of the separated polar phase may be recycled into the vegetable oil refining step according to the present invention.

The most important advantages of the transesterification method according to the present invention are as follows:
- transesterification reaction and phase separation proceed quickly;
- the amount of alkanol required for transesterification may be reduced considerably;
- only simple apparatuses are required;
- the required 95-98% conversion rate may also be attained without an intermittent stopping of the transesterification process, separating the phases, and performing a repeated transesterification;
- refining of the end product is simpler;
- the solvent and the non-reacted reactants may be recovered easily and may be recycled;
- a biodiesel fuel with an even quality may be produced;
- using appropriately selected aliphatic hydrocarbon solvents, quality improving additives may simultaneously be introduced into the biodiesel fuel product.

Further details of the present invention are illustrated with the aid of the following non-limiting examples.

EXAMPLE 1

400 ml of cold pressed sunflower oil (kinematic viscosity at 40° C.: 32 mm$^2$/s; acid number: 1.2 mg KOH/g), 175 ml of an aliphatic hydrocarbon fraction obtained in mineral oil distillation (boiling range: 75-95° C.; amount of aromatics: less than 1%), and a mixture of 40 ml of glycerol and 5 ml of water were fed into a container fitted with a stirrer, and the contents of the container were stirred for 20 minutes at a rate of 120 rpm. Stirring was stopped, and the contents of the container were allowed to stand for 30 minutes. The separated lower polar phase, which comprises the glycerol, the water and all impurities removed by them, was removed through a discharging unit fitted to the bottom of the container, and the upper apolar phase, comprising 96% of the introduced vegetable oil and aliphatic hydrocarbon solvent, was placed into a four-necked flask equipped with a stirrer, a reflux condenser, a thermometer and a dropping funnel. Sample was taken from the upper apolar phase for analysis, and the solvent was removed. According to the results, the kinematic viscosity of the thus refined solvent-free vegetable oil decreased to 24 mm$^2$/s (measured at 40° C.); its acid number decreased to 0.1 mg KOH/g.

In a separate flask, 2 g of potassium hydroxide was dissolved in 125 ml of methanol, and 75 ml portion of the resulting solution was placed into the dropping funnel. The substance filled into the four-necked flask was heated to a temperature of about 60° C. under stirring at a rate of 120 rpm, and then the methanol solution of potassium hydroxide was added drop-wise. The progress of transesterification was coupled with a slight increase in temperature. When the addition of the methanol solution was complete (which required 10 minutes), the temperature of the reaction mixture rose to 68° C.; thus the reaction reached the equilibrium within 10 minutes. Heating was switched off, and the reaction mixture, cooled to 50° C., was filled into a separation funnel. The lower polar phase fully separated from the upper apolar phase within 12 minutes. The lower polar phase comprising glycerol was set aside, and the upper apolar phase was refilled into the four-necked flask. The remainder of the methanol solution of potassium carbonate (50 ml) was filled into the dropping funnel, and transesterification of the apolar phase was continued as described above. Full transesterification was attained within 7 minutes. The contents of the flask were filled into a separation funnel, and the phases were allowed to separate at room temperature. Full separation of the phases required 120 minutes.

After both transesterification steps, samples were taken from the upper apolar phase, the aliphatic hydrocarbon solvent was removed from the samples by distillation, and then the samples (termed as "biodiesel phase" in Table 1) were analyzed. The results are indicated in Table 1, where the respective data of the starting sunflower oil and the refined sunflower oil are also given for comparison purposes.

TABLE 1

|  | Starting sunflower oil | Refined sunflower oil | Biodiesel phase |
|---|---|---|---|
| Conversion |  |  | Step 1: 88.8%<br>Step 2: 97.9% |
| Viscosity at 40° C., mm$^2$/s | 32 | 24.1 | Step 1: 6.16<br>Step 2: 4.57 |
| Acid number, mg KOH/g | 1.18 | 0.1 | Step 1: 0.2<br>Step 2: 0.2 |
| Density at 20° C., g/cm$^3$ | 0.921 | 0.907 | Step 1: 0.892<br>Step 2: 0.881 |

EXAMPLE 2

The procedure of Example 1 was followed with the difference that after both transesterification steps, the biphasic mixture was passed through 15 g of an anion-exchange resin in order to accelerate phase separation. Thus the time required for full separation of the phases (indicated by full transparency of the upper phase) decreased for Step 1 to 8 minutes and for Step 2 to 48 minutes. Upon this operation, the acid number of the biodiesel phase also decreased to 0.1 mg KOH/g. Kinematic viscosity of the biodiesel phase obtained in Step 2 was 4.46 mm$^2$/s (measured at 40° C.). Its density was 0.880 g/cm$^3$ (measured at 20°), which, compared with the respective data of Table 1, indicates that, regarding the characteristics decisive from the aspects of usability, biodiesel fuel may be prepared by the method of the invention in a steady quality.

EXAMPLE 3

One boring each was formed on the bottom and on the middle of the sidewall of a three-necked flask of 2 liters capacity, and pipelines for material supply, equipped with a closing valve, were fitted to the individual borings. A collector flask was placed below the pipeline fitted to the boring on the bottom. A tube equipped with a heating jacket was joined through a centrifugal pump to the pipeline fitted to the boring on the sidewall, and the tube was filled with 25 g of anion exchange resin. A pipeline was joined to the upper end of the tube, which was connected to one of the necks of the flask. Thus the assembly shown in FIG. 1, comprising a receiver 1 and a static mixer 2 connected thereto as a bypass, was formed. The flask was fitted with a thermometer and a reflux condenser. 1100 ml of a mixture of refined sunflower oil and aliphatic hydrocarbon solvent, obtained as described in Example 1, and a solution of 4 g of potassium hydroxide in 250 ml of methanol were filled into the flask. A completely homogeneous monophasic liquid was obtained. Water heated to 75° C. was circulated in the heating jacket of the static mixer 2 (i.e. of the tube filled with anion exchange resin), but the flask itself was not heated. The contents of the flask were circulated through the static mixer 2 at a rate of 50 l/min with the centrifugal pump. Upon the substance stream being re-circulated into the flask, the temperature in the flask started to rise. When the temperature rose above 45° C., the separation of a polar lower phase was already well observable. When the temperature in the flask reached 65° C., the closing valve attached to the lower boring was opened, a part of the separated polar phase was removed, and the separated polar phase was removed further at a rate of its formation by adjusting appropriately the closing valve. Steady state, as indicated by no further polar phase separates being formed, was reached within 37 minutes. At this time, the lower closing valve was closed. Circulation through the static mixer 2 was continued for a further 10 minutes, then circulation was stopped, the contents of the flask were allowed to cool to room temperature, and from that time, it was allowed to stand at room temperature for 1 hour. Thereafter the lower polar phase was removed through the lower closing valve, and the solvent was removed from the upper apolar phase which remained in the flask. Biodiesel fuel was obtained with a conversion rate of 96%. Quality characteristics of the product were as follows: kinematic viscosity at 40° C.: 4.36 mm$^2$/s; density at 20° C.: 0.876 g/cm$^3$; acid number: 0.17 mg KOH/g.

EXAMPLE 4

The procedure of Example 3 was followed with the difference that potassium hydroxide used as catalyst was replaced by an equivalent amount of sodium hydroxide. Under such conditions steady state was attained within 52 minutes, and the repose period required for full phase separation rose from 1 hour to 1.7 hours. The biodiesel fuel was obtained with a conversion rate of 96%. Quality characteristics of the product were as follows: kinematic viscosity at 40° C.: 4.54 mm$^2$/s; density at 20° C.: 0.884 g/cm$^3$; acid number: 0.25 mg KOH/g.

EXAMPLE 5

The procedure of Example 3 was followed with the difference that Blaugel® (a silica gel which indicates water saturation by color change) was filled into the static reactor as packing instead of anion exchange resin. Under such conditions, steady state was attained within 41 minutes, and the two phases, as in Example 3, fully separated after standing at room temperature for 1 hour. The biodiesel fuel was obtained with a conversion rate of 95%. Quality characteristics of the product were as follows: kinematic viscosity at 40° C.: 4.49 mm$^2$/s; density at 20° C.: 0.880 g/cm$^3$; acid number: 0.18 mg KOH/g.

EXAMPLE 6

The procedure of Example 3 was followed with the difference that a four-necked flask was used, and a dropping funnel was fitted into one of the necks. No methanol solution of potassium hydroxide was filled into the flask, but a solution of 4.8 g of potassium hydroxide in 300 ml of methanol was introduced through the dropping funnel in 10 equal portions. The separated polar phase was removed before introducing the individual solution portions. The correct timing of removal of the lower polar phase was determined by the onset of steady state (no more glycerol separates). The biodiesel fuel was obtained with a conversion rate of 98%. Quality characteristics of the products were as follows: kinematic viscosity at 40° C.: 4.38 mm$^2$/s; density at 20° C.: 0.879 g/cm$^3$; acid number: 0.14 mg KOH/g.

EXAMPLE 7

The procedure of Example 1 was followed with the difference that transesterification was performed in a pressurized reactor at 114° C. under a pressure of 24 bar. The 75 ml portion of the 125 ml methanol solution of potassium hydroxide was directly filled into the reactor. The reaction mixture was stirred with a magnetic stirrer. After reaching the required temperature, the mixture was stirred for 10 minutes. Stirring was then stopped, the temperature of the reactor was lowered to 50° C. and the pressure was lowered to atmospheric, and the contents of the reactor were filled into a separation funnel. An immediate full phase separation was observed, which indicates that the time elapsed after stopping of stirring (about 5-10 minutes) was sufficient to attain full phase separation. The conversion rate of transesterification (measured in the upper apolar phase after removing the solvent) was 92%. Quality characteristics of the substance were as follows: kinematic viscosity at 40° C.: 5.87 mm$^2$/s; acid number: 0.29 mg KOH/g.

Upon subjecting the upper apolar phase to repeated transesterification, the biodiesel fuel was obtained with a conversion rate of 98%. Quality characteristics of the product were as follows: kinematic viscosity at 40° C.: 4.38 mm$^2$/s; density at 20° C.: 0.879 g/cm$^3$; acid number: 0.14 mg KOH/g.

EXAMPLE 8

Used frying oil was filtered to remove solid impurities amounting to about 3%. 400 ml of the resulting filtrate (kinematic viscosity at 40° C.: 39.8 mm$^2$/s; acid number: 3.55 mg KOH/g) were refined as described in the first part of Example 1. Sample was taken from the upper apolar phase obtained in the refining step, and the aliphatic hydrocarbon solvent was removed from the sample. The kinematic viscosity of the resulting refined vegetable oil decreased to 25.6 mm$^2$/s (measured at 40° C.), its acid number decreased to 0.38 mg KOH/g. No filtration residue was obtained upon filtering the refined vegetable oil.

Thereafter the two-step transesterification procedure described in Example 1 was repeated with the apolar upper phase obtained in the refining step. The conversion attained in the second transesterification step was 96%. Quality characteristics of the product were as follows: kinematic viscosity at 40° C.: 4.66 mm$^2$/s; density at 20° C.: 0.881 g/cm$^3$; acid number 0.1 mg KOH/g.

What we claim is:
1. A biodiesel production method, comprising:
(a) providing a homogeneous reaction mixture in a first apolar phase, the reaction mixture comprising:
a refined vegetable oil;
a C1-C4 alcohol;
a catalyst, and
an aliphatic hydrocarbon solvent with a boiling point of 40-200° C.;
(b) allowing the refined vegetable oil to undergo transesterification whilst maintaining a homogeneous mixture comprising transesterified fuel, non-transesterified veg- etable oil and aliphatic hydrocarbon solvent in said first apolar phase; and forming a first polar phase comprising glycerol by-product;

(c) separating the first apolar phase and the first polar phase; and (d) refining the transesterified fuel from the first apolar phase, wherein the C1-C4 alcohol is used in an amount selected from the group consisting of: a stoichiometric amount; and an excess not exceeding 30% of a stoichiometric amount, and the aliphatic hydrocarbon solvent is used in an amount of at least 0.2 parts by volume relative to the unit volume of the refined vegetable oil.

2. The method according to claim 1, further comprising:

(a) reacting the first apolar phase with a C1-C4 alcohol in the presence of a catalyst to provide a second polar phase and a second apolar phase until a transesterification conversion rate of 95-98% is obtained;

(b) separating the second polar phase comprising glycerol by-product from the second apolar phase comprising the fuel; and (c) refining the second apolar phase to provide the fuel.

3. The method according to claim 1, wherein 0.3-1 parts by volume of the aliphatic hydrocarbon solvent is used for unit volume of the refined vegetable oil.

4. The method according to claim 1, wherein 0.4-0.7 parts by volume of the aliphatic hydrocarbon solvent is used for unit volume of the refined vegetable oil.

5. The method according to claim 1, wherein a substance having a boiling point range between 60-180° C. or a mixture of such substances is used as the aliphatic hydrocarbon solvent.

6. The method according to claim 1, wherein a mineral oil of low aromatic content having a boiling point range of 60-100° C. is used as the aliphatic hydrocarbon solvent.

7. The method according to claim 1, wherein a mineral oil of low aromatic content having a boiling point range of 100-140° C. is used as the aliphatic hydrocarbon solvent.

8. The method according to claim 1, wherein a mineral oil of low aromatic content having a boiling point range of 140-180° C. is used as the aliphatic hydrocarbon solvent.

9. The method according to claim 1, wherein the transesterification is performed at a temperature of 60-140° C. under a pressure sufficient for maintaining the C1-C4 alcohol in liquid state.

10. The method according to claim 1, wherein the transesterification is performed at a temperature of 95-115° C. under a pressure sufficient for maintaining the C1-C4 alcohol in liquid state.

11. The method according to claim 1, wherein methanol is used as the C1-C4 alcohol.

12. The method according to claim 1 further comprising a pre-transesterification step of refining a non-refined vegetable oil, the pre-transesterification step comprising:

mixing unit volume of a non-refined vegetable oil with at least 0.2 parts by volume of an aliphatic hydrocarbon solvent having a boiling point of 40-200° C. and 0.07-0.2 parts by volume of an aqueous glycerol comprising 5-40% by volume of water;

allowing the mixture to settle to form an upper apolar phase comprising a refined vegetable oil and the aliphatic hydrocarbon solvent and a lower polar phase, and removing the lower polar phase.

13. The method according to claim 12, wherein the water introduced into the apolar phase is removed by subjecting the apolar phase to azeotropic distillation in the presence of the aliphatic hydrocarbon solvent.

14. The method according to claim 1, wherein the transesterification is performed in an assembly comprising:

(a) a receiver;

(b) a static mixer coupled to the receiver; and (c) at least one pipeline, as a bypass, that couples the receiver and the static mixer to each other, wherein the receiver is maintained at ambient temperature and pressure, wherein the temperature and the pressure in the static mixer may be adjusted to those required for the transesterification reaction, wherein a mixture of the refined vegetable oil, the C1-C4 alcohol, the aliphatic hydrocarbon solvent, and the catalyst are fed into the receiver, and wherein portions of the mixture fed into the receiver are circulated through the static mixer at a rate which enables transesterification to proceed at least partially in the static mixer.

15. The method according to claim 14, further comprising:

(a) feeding the C1-C4 alcohol and the catalyst into a mixture exiting the receiver before the mixture enters the static mixer until a transesterification conversion rate of 95-98% is obtained, wherein the mixture comprises the refined vegetable oil and the aliphatic hydrocarbon solvent;

(b) stopping the feeding of the C1-C4 alcohol and the catalyst into the mixture; and (c) removing a polar phase separated at the bottom of the receiver.

16. The method according to claim 15, wherein portions of the polar phase separated at the bottom of the receiver are also separated during the feeding of the C1-C4 alcohol and the catalyst into the mixture comprising the refined vegetable oil and the aliphatic hydrocarbon solvent.

17. The method according to claim 1, wherein the catalyst is selected from the group consisting of: acid catalysts; and basic catalysts.

18. The method according to claim 17, wherein the catalyst is a basic catalyst selected from the group consisting of: potassium hydroxide; and sodium hydroxide.

* * * * *